(12) United States Patent
Alfano et al.

(10) Patent No.: US 10,426,349 B2
(45) Date of Patent: Oct. 1, 2019

(54) RESONANCE RAMAN SPECTROSCOPY ANALYZER INSTRUMENT FOR BIOMOLECULES IN TISSUES AND CELLS

(71) Applicant: Robert R. Alfano, Bronx, NY (US)

(72) Inventors: Robert R. Alfano, Bronx, NY (US); Cheng-hui Liu, Flushing, NY (US)

(*) Notice: Subject to any disclaimer, the term of this patent is extended or adjusted under 35 U.S.C. 154(b) by 332 days.

(21) Appl. No.: 15/243,391

(22) Filed: Aug. 22, 2016

(65) Prior Publication Data

US 2017/0049327 A1 Feb. 23, 2017

Related U.S. Application Data

(60) Provisional application No. 62/283,066, filed on Aug. 20, 2015.

(51) Int. Cl.
*A61B 5/00* (2006.01)
*A61B 1/07* (2006.01)
(Continued)

(52) U.S. Cl.
CPC ........ *A61B 5/0075* (2013.01); *A61B 1/00009* (2013.01); *A61B 1/00082* (2013.01); *A61B 1/00089* (2013.01); *A61B 1/051* (2013.01); *A61B 1/063* (2013.01); *A61B 1/07* (2013.01); *A61B 5/0042* (2013.01); *A61B 5/0086* (2013.01); *A61B 5/0091* (2013.01);
(Continued)

(58) Field of Classification Search
CPC ... A61B 5/0075; A61B 5/0042; A61B 5/4318; A61B 5/42; A61B 5/202; A61B 5/201; A61B 5/08; A61B 5/0091; A61B 10/0041; A61B 1/051; A61B 1/063; A61B 1/00089; A61B 1/00082; A61B 1/00009; A61B 1/07; A61B 5/0086; A61B 5/7282

See application file for complete search history.

(56) References Cited

U.S. PATENT DOCUMENTS 5,261,410 A * 11/1993 Alfano ................. A61B 5/0075
250/339.12
5,293,872 A 3/1994 Alfano
(Continued)

OTHER PUBLICATIONS www.breastcancer.org/symptoms/understand_bc/statistics.jsp Mar. 14, (2012).
(Continued)

*Primary Examiner* — Rex R Holmes
(74) *Attorney, Agent, or Firm* — Myron Greenspan Lackenbach Siegel LLP

(57) ABSTRACT

A method to detect vibrations associated with biomolecules in tissues and cellsuses Resonance Raman (RR) spectroscopy to measure specific biomolecules in tissue and cells signals. The changes of RR lines of key molecules present to the chemical conformations and change due to disease such as cancer and heart disease. Biomolecules are collagen, flavins, tryptophan, NADH, NAD, etc. The laser beams excite RR of vibration associated with absorption of the key native molecules in tissue (Tryptophan, NADH, Flavins, Collagen, carotenoids, porphyrins and others. The margin assessment and RR images in 2D and 3D regions are found by RR signals using position scanners. The intensity and the numbers of molecule fingerprints indicate the presence of and the degree of the changes of chemical conformations.

9 Claims, 7 Drawing Sheets

(51) Int. Cl.
| | |
|---|---|
| A61B 1/00 | (2006.01) |
| A61B 1/06 | (2006.01) |
| A61B 1/05 | (2006.01) |
| A61B 5/08 | (2006.01) |
| A61B 5/20 | (2006.01) |
| A61B 10/00 | (2006.01) |

(52) U.S. Cl.
CPC .............. *A61B 5/08* (2013.01); *A61B 5/201* (2013.01); *A61B 5/202* (2013.01); *A61B 5/42* (2013.01); *A61B 5/4318* (2013.01); *A61B 5/7282* (2013.01); *A61B 10/0041* (2013.01)

(56) References Cited

U.S. PATENT DOCUMENTS

| | | | | |
|---|---|---|---|---|
| 5,371,368 | A * | 12/1994 | Alfano | A61B 5/0091 250/341.1 |
| 6,006,001 | A * | 12/1999 | Alfano | G02B 6/241 385/115 |
| 6,151,522 | A * | 11/2000 | Alfano | A61B 5/0075 356/301 |
| 6,560,478 | B1 | 5/2003 | Alfano | |
| 8,953,159 | B2 * | 2/2015 | Cunningham | G02B 1/005 356/301 |

OTHER PUBLICATIONS

M. Mehta, M.A. Vogelbaum, S. Chang, "Neoplasms of the central nervous system", In: DeVita VT Jr, Lawrence TS, Rosenberg SA: Cancer: Principles and Practice of Oncology. 9th ed. Philadelphia, Pa: Lippincott Williams & Wilkins, 1700-49 (2011).

S.F. Altekruse, C.L. Kosary, M.Krapcho, "Seer Cancer Statistics Review", Bethesda, MD: National Cancer Institute, 1975-2007 (2010). [http://seer.cancergov/csr/1975_2007/].

J. Ferlay, H.R. Shin, F. Bray, "Globocan 2008: Cancer Incidence and Mortality Worldwide IARC Cancer Base No. 10", in Lyon, France: (2008).

Haka A.S., Volynskaya Z., Gardecki J.A., Nazemi J., Lyons J., Hicks D. In vivo Margin Assessment during Partial Mastectomy Breast Surgery Using Raman Spectroscopy, Cancer Res 66: (6). Mar. 15, 3317-3322 (2006).

S.H. Taghipour Zahir, M. Rezaei sadrabadi, F. Dehghani, "Evaluation of Diagnostic Value of CT Scan and MRI in Brain Tumors and Comparison with Biopsy", Iranian Journal of Pediatric Hematology Oncology, 1(4), 121-125 (2011).

F. H. Gilles, W.D. Brown, A. Leviton, C.J. Tavare, L. Adelman, L.B. Rorke, et al , "Limitations of the World Health Organization classification of childhood supratentorial astrocytic tumors. Children Brain Tumor Consortium", Cancer Mar. 15; 88(6), 1477-83 (2000).

Pripotnev S., Tsopmo A., Frielb J. and Ianoul K. UV resonance Raman spectroscopy probes the amide II peak position in short breast milk peptides with antioxidant activity, J. Raman Spectrosc., 42, 2105-2111 (2011).

Adar F. and Erecifiska M., Photoreductive titration of resonance Raman spectra of cytochrome oxidase in whole mitochondria, Biochemistry, Vo. 18, No. 9, 1825-1829 (1979).

Sharp MG, Adams SM, Walker RA, Brammar WJ, Varley JM, Differential expression of the mitochondrial gene cytochrome oxidase II in benign and malignant breast tissue. J Pathol 168:163-168 (1992).

Steinke J.M. and Shepherd A.P Effects of temperature on optical absorbance spectra of oxy-, carboxy-, and deoxyhemoglobin, Clin. Chem. 38/7, 1360-1364 (1992).

Esteve-Núñez A., Sosnik J., Visconti P. and Lovley D.R., Fluorescent properties of c-type cytochromes reveal their potential role as an extracytoplasmic electron sink in Geobacter sulfurreducens, Environmental Microbiology 10(2), 497-505 (2008).

Yan Zhou, Cheng-Hui Liu, Yi Sun, Yang Pu, Susie Boydston-White, Yulong Liu and Robert R. Alfano, "Human Brain Cancer Studied by Resonance Raman Spectroscopy", submitted to Journal of Biomedical Optics, (2012).

C.-H. Liu, Y. Zhou, Y. Sun, J. Y. Li, L. X. Zhou, S. Boydston-White, V. Masilamani, K. Zhu, Y. Pu, and R. R. Alfano, "Resonance Raman and Raman Spectroscopy for Breast Cancer Detection", submitted to special section on Raman TCRT (2012).

Yen Zhou, Cheng-hui Liu, Jiyou Li, Lixin Zhou, Yi Sun, Yang Pu, Ke Zhu, Yulong Liu, Qingbo Li, Gangge Cheng and Robert R. Alfano, "Resonance Raman spectroscopy for human cancer detection of key molecules with clinical diagnosis" SPIE: 8577-10, PW138-BO206-12 (2013).

R. R. Alfano, D. Tata, J. Cordero, P. Tomashefsky, F. Longo, and M. Alfano, "Laser induced fluorescence spectroscopy from native cancerous and normal tissue", IEEE J. Quant. Electron, 20, 1507-1511 (1984).

R. R. Alfano, G. C. Tang, Asima Pradhan, W. Lam, Daniel S. J. Choy, Elena Opher, "Fluorescence Spectra from Cancerous and Normal Human Breast and Lung Tissues", IEEE J. of Quant. Electron QE, 23, 1806, (1987).

R.R. Alfano, C.-H. Liu, W.L. Sha, H.R. Zhu, D.L. Akins, J. Cleary, R. Prudente and E. Clemer, "Human breast tissues studied by IR Fourier transform Raman spectroscopy", Lasers Life Sci. 4, 23-8 (1991).

R. R. Alfano and Y. Yang, "Stakes shift emission spectroscopy of human tissue and key biomolecules," IEEE Quantum Electron, 9(2), 148-153 (2003).

C.-H. Liu, V. Sriramoju, W. B. Wang, M. Frankfurt, N. D. Zadeh, and R. R. Alfano, "Study of lipid rich compositions in the intimal wall of aorta by Raman spectroscopy", Proc. of SPIE vol. 6853, 6853 1E, (2008).

A. Pradhan, B.B. Das, C.H. Liu, R.R. Alfano, K.M. O'Brien, M.L. Stetz, J.J.Scott, L.I. Deckelbaum, "Time resolved Fluorescence of Normal and Atherosclerotic Arteries", SPIE vol. 1425 p. 2-5 Diagnostic and Cardiovascular Interventions (1991). Proc. of SPIE vol. 6853 68531E-3.

C.-H. Liu, W.L. Sha Glassman, H.R. Zhu, D.L. Akins, L.I. Deckelbaum, M.L. Stetz, K.O'Brien, L.Scott and R.R. Altana, "Near-IR Fourier Transform Raman Spectroscopy of Normal and Atherosclerotic Human Aorta", Lasers in the Life Sciences 4(3), p. 257-264 (1992).

J.T. Motz "Development of In Vivo Raman spectroscopy of atherosclerosis", Thesis, MIT pp. 183-204 (2003), J.T. Matz, M. Fitzmaurice, A. Miller, S.J. Gandhi, A.S. Haka, L.H. Galindo, R.R. Dasari, J.R. Kramer and M.S. Feld, "In Vivo Raman spectral pathology of human atherosclerosis and vulnerable plaque", J. Biomedical Optics 11(2), pp. 021003-1-9 (2006).

H. Abramczyk, B. Brozek-Pluska, J. Surmacki, J. Jablonska-Gajewicz and R. Kordek, Raman 'optical biopsy' of human breast cancer, Progress in Biophysics and Molecular Biology, vol. 108, 74-81 (2012).

M.F. Kircher, Adam de la Zerda, Jesse V Jokerst, Cristina L Zavalet, Paul J Kempen, Erik Mittr, Ken Pitter, Ruimin Huang, Carl Campos, Frezghi Habt, Robert Sinclair, Cameron W Brennan, Ingo K Meliinghoff, Eric C Holland & Sanjiv S Gambhir, A brain tumor molecular imaging strategy using a new triple-modality MRI-photoacoustic-Raman nanoparticle, Nature Medicine vol. 18, No. 5, May (2012).

\* cited by examiner

RESONANCE RAMAN SPECTROSCOPY ANALYZER INSTRUMENT FOR BIOMOLECULES IN TISSUES AND CELLS

BACKGROUND OF THE INVENTION

1. Field of the Invention

The invention generally relates to methods of detection of cancer and, more specifically, to a Resonance Raman spectroscopy analyzer instrument for biomolecules in tissues and cells.

2. Description of Prior Art

Breast cancer is one of the major causes of death in women. Early diagnosis has increased the five-year survival rate of cancer patients. In 2011, approximately 230,480 new cases of invasive breast cancer in women were diagnosed in United States (US), and 57,650 new cases of noninvasive breast cancer. The mortality rate in women due to breast cancer is second only to lung cancer in the US [1]. Brain tumors represent 85-90% of the tumors found in the primary central nervous system tumors. In 2011, 22,910 new cases were diagnosed and 13,700 deaths from brain and other nervous system cancers were reported in the United States and in 2008, approximately 238,000 new cases of brain and other central nervous system (CNS) tumors were diagnosed worldwide, with an estimated 175,000 deaths [2-4].

Today, human cancer of breast or brain screening and diagnosis are performed by a combination of the physician's search for palpable lesions adding visual inspection and physical in situ detection e.g. X-ray (mammography for breast), ultrasonography (US), X-ray computed tomography (CT), optical coherence tomography (OCT), magnetic resonance imaging (MRI), and positron emission tomography (PET), then followed by one or more tissue biopsies.

These methods cannot provide reliable diagnosis and invasive traditional clinical diagnostics have limitations in sensitivity and accuracy, and give little or no information regarding molecular and cellular change and mechanisms. For example, for breast lesions: seventy to ninety percent of the suspicious lesions detected by mammography are determined to be benign lesions upon biopsy. However, 20% of the malignant lesions go undetected by mammography [5]; for brain lesions: in early diagnosis, histochemical analysis by a pathologist results in a 90% detection rate from brain tissue biopsies. While CT and MRI imaging are predicative for locating intracranial tumors, the accuracy of these imaging methods for diagnosis inferior to histochemical analysis, with a diagnostic accuracy of 66% and 63%, respectively, according to a 1995 report [6-7].

Minimally-invasive or noninvasive optical spectroscopy techniques for the diagnosis of suspicious lesions in real-time could reduce patient trauma and discomfort, time to diagnosis, and the high medical costs in comparison with traditional biopsy.

Optical spectroscopy methods such as Raman spectroscopy, Raman CCD spectroscopy (RS), fluorescence (FL) spectroscopy and Stokes shift spectroscopy (SSS) have widely been used to diagnose human diseases reported since the late 1980's [18-21]. Since fluorescence spectra of tissue involve emissions from various molecules and are usually broad, it is difficult to use FL spectra to distinguish contributions from each of the involved molecules. Raman spectra provide narrow spectral features that can be related to the specific molecular structure even for complex multi-component samples such as biological tissues. The detailed biological information obtained from Raman spectra is suitable for histochemical analysis and lesions diagnosis of the human tissue. Many groups have recognized the potential of Raman spectroscopy in the study and diagnosis of cancer diseases and have been made many progresses in the analysis of normal and diseased tissues in vitro and in vivo using Raman spectroscopy [22-26]. It has been reported that Raman spectroscopy as a non-destructive optical technique can provide histochemical information in molecular level about contents of proteins and DNAs in human tissues [27-28].

Raman spectroscopy has received increasing attention over past several years as a tool for use in examining human breast, artery diseases and other biological materials. An example of Raman spectroscopy used to the examination of human breast, Alfano et al., U.S. Pat. No. 5,261,410, Nov. 16, 1993 [17] describes a method for determining if a tissue is a malignant tumor tissue, a benign tumor tissue, or a normal benign tissue using Raman Spectroscopy. Alfano et al., in U.S. Pat. No. 6,151,522 and in U.S. Pat. No. 6,560,478B [29-30], described novel method and system employing a low-power continuous wave (cw) pump laser beam and a low-power cw Stokes (or anti-Stokes) probe laser beam. The pump beam and the probe beam simultaneously illuminate the biological material and traverse the biological material in collinearity. The pump beam, whose frequency is varied, is used to induce Raman emission from the biological material. The intensity of the probe beam, whose frequency is kept constant, is monitored as it leaves the biological material. When the difference between the pump (Ω) and probe (ω) excitation frequencies is equal to a Raman vibrational mode frequency (ν) of the biological material, the weak probe signal becomes amplified by one or more orders of magnitude (typically up to about $10^4$-$10^6$) due to the Raman emission from the pump beam. In this manner, by monitoring the intensity of the probe beam emitted from the biological material as the pump beam is varied in frequency, one can obtain an excitation Raman spectrum for the biological material tested. This method may be applied to in the. in vivo and/or in vitro diagnosis of diabetes, heart disease, hepatitis, cancers and other diseases by measuring the characteristic excitation Raman lines of blood glucose, cholesterol, serum glutamic oxalacetic transaminase (SGOT)/serum glutamic pyruvic transaminase (SGPT), tissues and other corresponding Raman-active body constituents, respectively. Alfano's the (Mach 1994) U.S. Pat. No. 5,293,872 [16] describes method and apparatus for distinguishing between calcified atherosclerotic tissue or normal cardiovascular tissue using Raman spectroscopy. U.S. Pat. No. 5,293,872 is incorporated by reference as if fully set forth herein.

Accordingly, in view of the above, it can be seen that Raman spectroscopy with has been useful to detect changes in lesions. And the above-described techniques are enabling the use of fiber optic Raman spectroscopy for detection of the changes in cancer tissues and detection cancerous region. Tissues and cells from brain, breast, GYI (cervix, ovary, vuva), GI track (colon, stomach, rectum), urinary track and bladder can be probed by RR to find cancers.

A key limitation has been the lack of available technique with an appropriate indicator for probing the margin assessments during surgery in real time in vivo. Recently, a new method and system using fiber optic Raman probe-based clinical system to determine cancer composition changes in vitro were developed.

SUMMARY OF THE INVENTION

The invention teaches how to use new Raman method and system to detect RR vibrational modes of key molecules fingerprints of human tissues and cells using wavelengths of lasers below 640 nm within the region 500 cm-1 to 4000 cm-1 and others vibration modes of tissue with a laser excitation to detection with over lesion region of tissues to find lesion sites and region in the lesions. These laser wavelengths (<650 nm excites the key chromophores in tissues and vibrations about them for biomolecules of Tryptophan, collagen, NAD, NADH, flavins and porphyrins. This method can be used in vivo humans in situ. Tissues and cells from brain, breast, GYI (cervix, ovary, vuva), GI track (colon, stomach, rectum), urinary track and bladder can be probed by RR to find cancers. These RR modes reveal the strong vibration strength caused by the C—H, C—C, C═C, CH2, CH3, N—H, C—N, C═O, vibration bonds region of proteins and DNAs under the tissue. The intensity of the RR peaks as a function of the type of tissue was demonstrated. The study has demonstrated a very important application potential that the RR vibration bands of key molecules may be used as new indicators to monitor the changes of human lesions, and the stages of the transformation of human cells. It may also be used to monitor other effects of cancer therapy on development in vivo by combing this RR technology with calculated Bayes and SVM methods we can find both type of lesions (classification). Different lasers and SHG beams from 300 nm to 640 nm—blue to red to NIR can be used for RR (i.e. Argon, semiconductor lasers, YAG, fiber lasers, He—Ne, Dye, Ti: Sapphire, Forsterite, Cunyite, LIGO, LISO) can be used to detect the key molecular modes in other organs by RR.

The experimental results show that the changes of intensities of characteristic RR spectral modes of the breast and brain tissues were in cancer and benign tissues. A classification curves were used in displaying the cells transformed processes indicating that the conformation changes of tissue could be detected if mixture tissues is considered. The RR modes of key molecules as new indicators of lesion sites may provide as a new probe in simple system for clinical applications to detect cancer in vivo in human tissues and other organs such as from brain, breast, GYI (cervix, ovary, vuva), GI track (colon, stomach, rectum), lung, kidney, urinary track and bladder.

This study and teachings opens up new method of using RR spectroscopy to detect and monitor human diseases and to locate cancer at earlier stage at least. The intensity or ratio of these RR vibrational modes may be used as new indicators to predict the changes of the composition of the human tissues, and monitor the changes of cells at different types of cancer and stages.

BRIEF DESCRIPTION OF THE FIGURES

The above and other aspects, features and advantages of the present invention will be more apparent from the following description when taken in conjunction with the accompanying drawings, in which.

DETAILED DESCRIPTION OF THE INVENTION

Figure 1:
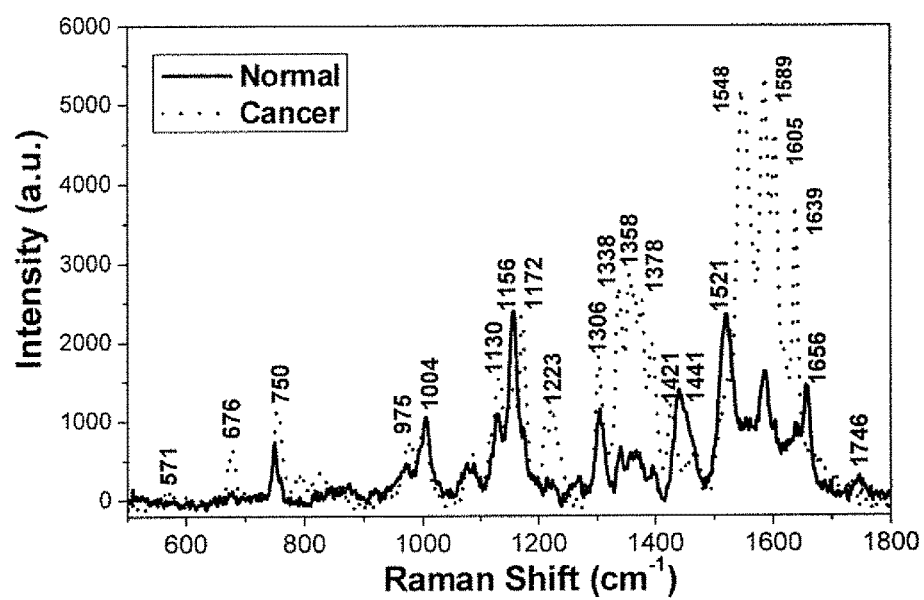
FIG. 1 is the graphic representations of signals produced under the RR conditions in short wavelength scan region. The typical RR spectra of normal and cancer (IDC stage II) breast tissues over the range 500 cm$^{-1}$ to 1800 cm$^{-1}$ were plotted. The exposure time was 30 seconds.

The early stage of cancer in human tissue is found by using specific bio-molecular vibrational fingerprints model by Resonance Raman (RR) spectroscopy. The key molecular fingerprints with enhance vibrational modes were measured using confocal micro Raman system. The key is the laser source wavelength is near an absorption in tissue to be enhanced by 10 to 1000 fold. The tissues of breast and brain lesions and 532 nm were use as a model to laid the founding principles in clinical diagnosed by histological and immunohistochemistry morphological technique. The RR spectra of cancer, benign and normal breast and brain tissues were investigated. The changes of intensities of the Raman modes arising from key molecules were found. SVM and Bayes classification models based on statistical methods were performed on RR spectral data. The results revealed the components changes and classified between cancer and normal human lesion tissues.

The present invention relates to the new method of detecting and predicting cancer sits and regions from its vibration states, with in the tract composition at earlier stage, the transformed cells and development and using the map of the transformed cells changes in vary with lesions of type of cancers. The present application extends the teaching of Alfano's U.S. Pat. Nos. 5,293,872 and 5,261,410 [16-17] by detecting vibrations using RR modes of lesions and have added new probe indicators at RR modes of key molecules fingerprints and RR system designs to find lesion region of the tissue region using fiber optic based RR system.

A RR ratio meter is used to measure Raman mode intensity at two or more RR frequencies to get the key molecules fingerprints in tissues and may reveal the molecular order ratio. The sharp bands of cancer tissues at centered e.g. about 750 $cm^{-1}$, 1004 $cm^{-1}$, 1156 $cm^{-1}$, 1358 $cm^{-1}$, 1589 $cm^{-1}$, and bands at 2850 $cm^{-1}$, 2935 $cm^{-1}$ for breast cancer, the RR sharp bands locate in malignant meningioma brain cancer tissues are at 750 $cm^{-1}$, 1004 $cm^{-1}$, 1156 $cm^{-1}$, 1358 $cm^{-1}$, 1548 $cm^{-1}$, and 2891 $cm^{-1}$ and 2934 $cm^{-1}$; the distinct RR lines at 752 $cm^{-1}$, 1004 $cm^{-1}$, 1172 $cm^{-1}$, 1358 $cm^{-1}$, 1585 $cm^{-1}$, and 2935 $cm^{-1}$, 2888 $cm^{-1}$ for glioma malignant tissue. So, detection at ratios or intensities can be integrated or only peak intensity. The peaks and shapes vary from sample to sample to locate cancer.

We have developed a method and system to detect the human lesions using RR spectroscopic technique where the salient features are the key vibrations of key modes of molecule fingerprints from the tissues.

This invention of RR is based on new research that teaches:

1. The main characteristic fingerprint RR vibrational modes of cancer and normal breast tissue were found: e.g. at 1156 $cm^{-1}$, 1521 $cm^{-1}$, 2854 $cm^{-1}$ and 3013 $cm^{-1}$ were detected in the spectra of normal breast tissues that were stronger in intensity in comparison with those in the spectra of cancerous breast tissue. In the RR, the spectral wing is weaker than Vibrations from RR over conventional which require an algorithm to subtract off the wing when using non RR for 785 nm radiation to excite Raman spectra. In RR, about twelve dramatically enhanced characteristic vibrational peaks, including the enhanced amide II peak at 1548 $cm^{-1}$ in the spectra of cancerous breast tissues, distinguished the cancerous tissue from the normal tissues. Amide is not allowed in conventional Raman. The intense resonance enhancement displayed in two groups of peaks: one at 1338 $cm^{-1}$-1378 $cm^{-1}$ and the second group at 1548 $cm^{-1}$-1605 $cm^{-1}$, These resonance enhancements suggest that the 532 nm excitation wavelength matched (or closely matched) the molecular absorption wavelengths for molecular compounds in the cells and tissues. For example, the flavins, carotene, metalloprotein, hemoglobin, has one absorption band at 534 nm. Similarly, the mitochondrial electron transport protein, cytochrome c, has one absorption wavelength at 552 nm (under the hypoxia conditions), and other reason of the RR enhancement may be caused of generation of the two-photon absorption (TPA) process under RR conditions that contribution to RR enhancement especially for amino acids of proteins or DNA. The RR technique, using the 532 nm wavelength excitation, revealed key differences in the spectra of cancerous breast tissue vs. normal breast tissues, in peaks associated with proteins on the molecular level in cancer tissues and may have detected a greater contribution of some heme proteins, such as the cytochromes that reside in the mitochondria [8, 9-12].

2. The main characteristic fingerprint RR vibrational modes of cancer and normal brain tissue were found: using 532 nm excitation, the resonance enhanced peak at 1548 $cm^{-1}$ (amide II) was observed in all of the tissue specimens, but was not observed in the spectra collected by the non resonance Raman system. An increased in the peak intensity ratio of 1587 $cm^{-1}$ to 1605 $cm^{-1}$ was observed in the RR spectra collected from meningeal cancer tissue compared with the spectra collected from the benign and normal meningeal tissue. The peaks at 1732 $cm^{-1}$ are attributed to fatty acids (lipids) were diminished in the spectra from the meningeal cancer tumors compared to the spectra from normal and benign tissues. The characteristic band of spectral peaks observed between 2,800 $cm^{-1}$ and 3,100 $cm^{-1}$, are attributed to the vibrations of methyl (—$CH_3$) and methylene (—$CH_2$—) groups. The ratio of the intensities of the spectral peaks of 2935 $cm^{-1}$ to 2880 $cm^{-1}$ from the meningeal cancer tissues was found to be lower as compared to that of the spectral peaks from normal and benign tissues may be used as a distinct marker for distinguishing cancerous from normal meningeal tissues [13].

The results presented here demonstrate the potential of RR spectroscopy to successfully discriminate amongst normal brain tissues; cancerous brain tumors; and benign brain lesions using excitation wavelength at 532 nm. The use of other excitation using tunable or visible laser diodes can pump other the key proteins and amino acids and enhance the associated vibrational modes to give RR spectra. Using lasers near 340 nm excites collagen, near 380 nm excites elastin, near 450 nm excites NADH, and 500 nm excites flavins and carotene, The RR spectra from different types of brain tissue within vibrational spectral region 500 $cm^{-1}$ to 4000 $cm^{-1}$ were collected using confocal micro-Raman system and reported the first time.

The RR characteristic spectra of proteins (amides and amino acids) and type I, IV of collagen bands at 1088 $cm^{-1}$ and 1302 $cm^{-1}$ enhancement were found in the spectra collected from malignant meningioma tumor, diagnosed as grade III brain tissues. The first characteristic mode, an intense enhancement of amide II at 1547 $cm^{-1}$ might be used as an indicator of RR frequency using excitation wavelength at 532 nm. In the high frequency region between 2500 $cm^{-1}$ and 3500 $cm^{-1}$, bands due to symmetric stretch vibration, the peaks intensity ratio of methyl to methylene groups may suggest as a statistical method (a disorder/or order molecular conformation coefficient) to distinguish the spectra collected from malignant meningioma from normal meninges brain tissues. Normal meningeal brain tissue has a higher order coefficient compared with malignant meningioma meningeal tissue [14-15].

The key biomolecules fingerprints and ratios of RR vibrational modes are used to show a simple, less expensive and accurate optical technique for monitoring the degree of cancer cells transformation lesions where is the human lesions in nascent stages. A RR signal at 1548 $cm^{-1}$ indicates the presented of protein changes. This could also be ratio to detect the human lesions in nascent stages.

The RR modes are used as new molecular spectroscopic fingerprint indicators to monitor in situ the development of cancerous in human lesions, and determine the change at different stages of tissues to find margin assessments areas. When the changes of the RR signals are observed from the tissue is the transformed cells to be a region of cancer. Tissues and cells from brain, breast, GYI (cervix, ovary, vuva), GI track (colon, stomach, rectum), urinary track and bladder can be probed by RR to find cancers.

The method and the instrumental design for detecting and monitoring the changes of RR of key molecules fingerprints of human lesions by RR spectroscopic technology optical filtered fiber bundles (extension Alfano's patent [16-17]) are present here. This new method is based on our new finding of characteristic RR vibration bands of molecules fingerprints of human tissues used compare with RR mode strength for tissues can be used to detect cancer cells. The RR modes of key molecules fingerprints which are the main proteins and DNA vibration bands have sharp spectrum, strongly strength features and highly stability with varied environments including temperature as fingerprint of human tissues.

To test the RR spectroscopy of lesion to find cancer, the RR vibration modes e.g. at centered 750 cm$^{-1}$, 1004 cm$^{-1}$, 1156 cm$^{-1}$, 1358 cm$^{-1}$, 1589 cm$^{-1}$, and bands at 2850 cm$^{-1}$, 2935 cm$^{-1}$ for cancer and normal breast tissues were measured and investigated.

The RR vibrational modes for human diseases are strong bands of biomolecules of proteins and DNA at molecular vibrational fingerprints i.e.: carotenoids (1157 cm$^{-1}$, 1524 cm$^{-1}$), tryptophan, NADH (1548 cm$^{-1}$), tyrosine and phenylalanine (1605 cm$^{-1}$), FAD (1173 cm$^{-1}$), mitochondrial cytochromes (1587 cm$^{-1}$), collagen (1088 cm$^{-1}$) and elastin (1666 cm$^{-1}$) determine the regions of the transformation. We test our teachings the concept for RR spectroscopy for the first time on breast and brain tissues with confocal micro of Raman system using 532 nm laser excitation within the spectral scan region 200 cm$^{-1}$ to 5000 cm$^{-1}$ to see how to find diagnosis and treatment of cancer in nascent stages. Using other laser sources to excite near absorption to enhance other molecules in tissue by RR to give vibrational images associated with molecules. Tissues and cells from brain, breast, GYI (cervix, ovary, vulva), GI track (colon, stomach, rectum), urinary track and bladder can be probed by RR to find cancers and image margins and give a map of the vibrations in normal and cancer regions.

Method:
1. The huge databases of criterion assessments are founded. The method using RR modes from key molecules fingerprints: e.g. in centered at 1378 cm$^{-1}$, 1548 cm$^{-1}$, 1605 cm$^{-1}$, 2850 cm$^{-1}$ and in 2934 cm$^{-1}$ mode with the standard probe scanning to distinguish between the lesion tissue and normal tissue region, and determination the criterion assessments to find transformed cells.
2. The optical fiber bundles: one of the probe channels is designed to collect calibration signal.
3. Software is real time convert the signal from the probe scanning by calibration signal and plot the area the key molecular modes strength versus the standard value of under the lesion tissue to find regions and lesion's level of tissue using one or more lasers at different wavelengths;
4. Image and calculation results are showed on real time in the area of lesions, and on the changes of the level according to the criteria.
5. Measure Ratio at the RR peaks for key molecules fingerprint to human diseases.
6. Measure the peaks intensity at RR lines and bands for at least two more modes find out lesion and as the regions of lesions.
7. Smaller region about nano-meters to μms of tissue can be probe to detect the lesion regions by using RR spectra in the tissue such as green/blue lasers using semiconductor lasers, argon laser, or others.

We can detect the margin assessments within the microns with the cells mapping steps region. The RR spectra and the changes of intensities of RR modes reveal the degree (its developments), types, size and components of lesions of tissues according the detail criterion. If the changes of RR signals from the key molecules fingerprints in the tissue are observed the transformed cells is occurred and the tissue is a cancer. An optical fiber and Raman probe systems used detecting the laser and detect RR signals on lesions. The instrumental design of confocal micro Raman imaging system are consisting of a three-part Raman spectroscopic system, the light source of single mode lasers at 532 nm, 514.5 nm and 488 nm even with non resonance 633 nm and 785 nm and near IR wavelength or other wavelengths, backscattering signal optical fiber collection with spectrograph, CCD camera; xyz scanners for images of tissue vibrations, and a micro Raman imaging endoscope system which based on Alfano et al. in U.S. Pat. No. 5,293,872 [16] and others. The micro Raman endoscope system is consisting of single mode fiber, multiple heads of probe, side prisms and lenses, four-90° umbrella for screening blood or intervening fluid and cellular plasma, and added two arms fiber probes for calibrations key molecules and mixture components and tissues. Raman spectral resolution is ±2 cm$^{-1}$ or other. The detecting spot size may reach into the micron meter diameters, selecting laser wavelength at 532 nm, and blue 488 nm, 457 nm, 514 nm from Argon laser, semiconductor lasers YAG laser in SHG, He—Ne, tunable lasers, SHG (380 nm to 525 nm) from Ti Sapphire laser in 680 nm to 1,100 nm NIR region with SHG for 340 nm to 550 nm.

The excitation wavelength 532 nm (SHG Yag), 488 nm, 514 nm, He—Cd laser (at 325 nm and 442 nm); and 408 nm as excitation sources for Biomolecules in tissue to enhance the vibrations in RRS matched some molecular absorption bands generated resonance Raman effects on the human tissues. The RR spectral of key molecules fingerprints revealed the changes of transformed cells in lesion human tissues. In the present patent application, the design using fiber-optic probe based endoscopic system and using RR of key molecules modes of cancer tissues are reported to find transformation cells on lesions. The use of visible and UV is suitable for RR of biomolecules in tissue and cells to detect cancers in different organs and on skin. We show the use in RR of Brain and Breast.

Resonance Raman dispersion spectroscopy involves the measurement of resonance excitation and depolarization ratios of a large number of Raman lines at various excitation energies covering the spectral region of the chromophore's optical absorption bands. Resonance Raman spectroscopy is an ideal tool to investigate the structural properties of chromophores embedded in complex biological material environments. RR spectroscopy can enhance particular vibrational modes associated with key characterizing molecules excited with biological changes on molecular level with a higher resolution.

There are two possible resonances in the Stokes nonlinear polarization: one involving the vibrational state and one for electronic transitions in Raman process. The Stokes polarization [20] is:

$$\hat{P}_s = \sum_j |\hat{E}_L|^2 \hat{E}_s \frac{\mu_{0j}\mu_{j2}\mu_{20}}{4\hbar^2(\omega_{j0} - \omega_L)(\tilde{\omega}_{20} - \omega_q)(\omega_{j0} - \omega_L)} \quad (2)$$

where $\mu_{0j}$ is dipole transition from 0 ground state to j state, $\mu_{j2}$ is the dipole transition from j state to the 2 vibrational state, $\hat{E}_L$ is Laser electric field and $\hat{E}_s$ is the Stokes field. $\tilde{\omega}_{20} = \omega_{20} - i\Gamma_2$, where $\Gamma_2$ is the linewidth for the given state (one over the lifetime).

When the lasers ωL enters the absorption states j, the Stokes Polarization (cross section) increases due to the denominator approaches zero. This effect is Resonance Raman (RR) effect. In addition, when the ω20 approaches coq vibrational frequency, the middle term gets smaller and the polarization increases and can blow up and Raman of vibrations associated with these resonances are increased from 10 to 1000×. The Raman cross section increases when the energy denominator approaches zero and the Raman scatter intensity increases when the laser frequency approach a real absorbing state j of the native molecule in the tissue to enhance image of an near by or coupled vibration.

FIG. 1 shows RR spectra of normal and cancer (IDC stage II) breast tissues over the range of 500 cm$^{-1}$ to 1800 cm$^{-1}$.

Figure 2:
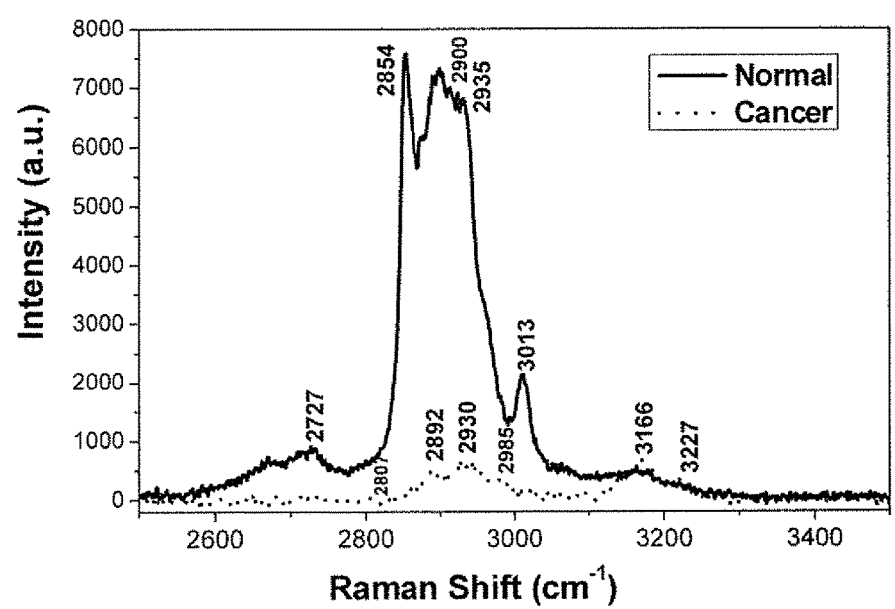
FIG. 2 is the graphic representations of signals produced under the RR conditions in longer wavelength scan region. The RR spectra of normal and cancer (IDC stage II) breast tissues over the higher wavenumber range of 2500-3500 cm$^{-1}$. The exposure time was 30 seconds.

FIG. 2 shows RR spectra of normal and cancer (IDC stage II) breast tissues over the higher wavenumber range of 2500-3500 cm$^{-1}$.

Figure 3:
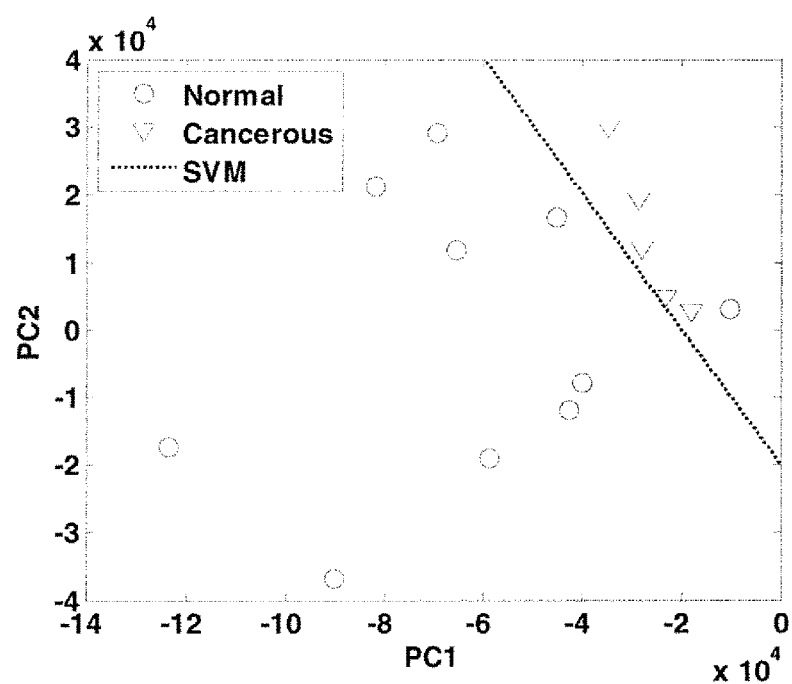
FIG. 3 is the graphic representations of signals produced under the RR conditions. The RR spectra of normal breast tissues and IDC breast cancer tissues projected onto the subspace spanned by the principal components (PCs)—PC 1 and PC 2—as diagnostically significant components.

FIG. 3 shows RR spectra of normal breast tissues and IDC breast cancer tissues projected onto the subspace spanned by the principal components (PCs)—PC 1 and PC 2—as diagnostically significant components.

Figure 4:
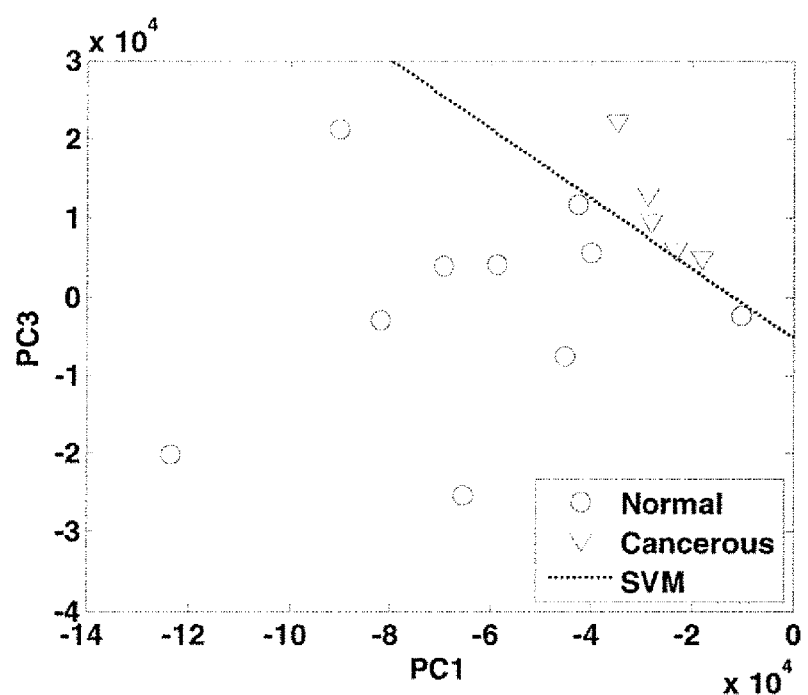
FIG. 4 is the graphic representations of signals produced under the RR conditions. The RR spectra of normal breast tissues and IDC cancer breast tissues projected onto the subspace spanned by the principal components (PCs)—PC 1 and PC 3—as diagnostically significant components.

FIG. 4 shows RR spectra of normal breast tissues and IDC cancer breast tissues projected onto the subspace spanned by the principal components (PCs)—PC 1 and PC 3—as diagnostically significant components.

Figure 5:
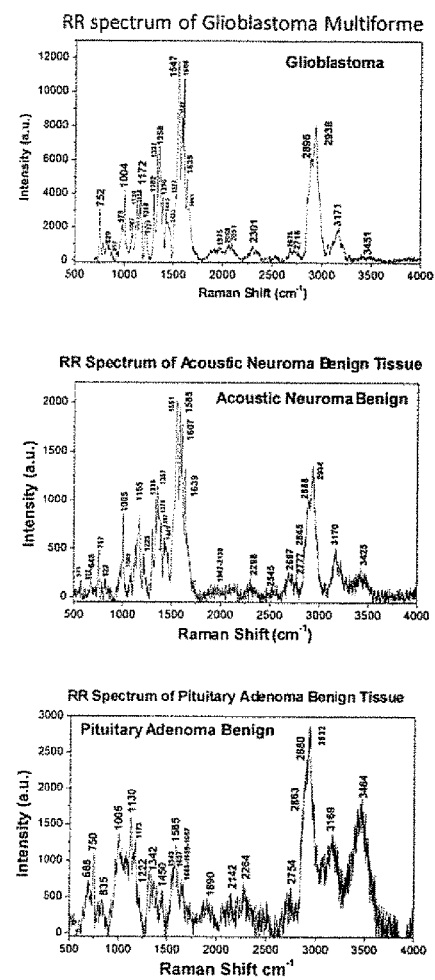
FIG. 5 is the graphic representations of signals produced under the RR conditions. The RR spectra recorded from three types of brain tissues. The top of Raman spectrum was from glioblastoma multiforme, grade IV tissue; the center of Raman spectrum was from acoustic neuroma benign tissue and the bottom of Raman spectrum was from pituitary adenoma benign tissues.

FIG. 5 shows RR spectra recorded from three types of brain tissues. The top of Raman spectrum was from glioblastoma multiforme, grade IV tissue; the center of Raman spectrum was from acoustic neuroma benign tissue and the bottom of Raman spectrum was from pituitary adenoma benign tissues.

Figure 6:
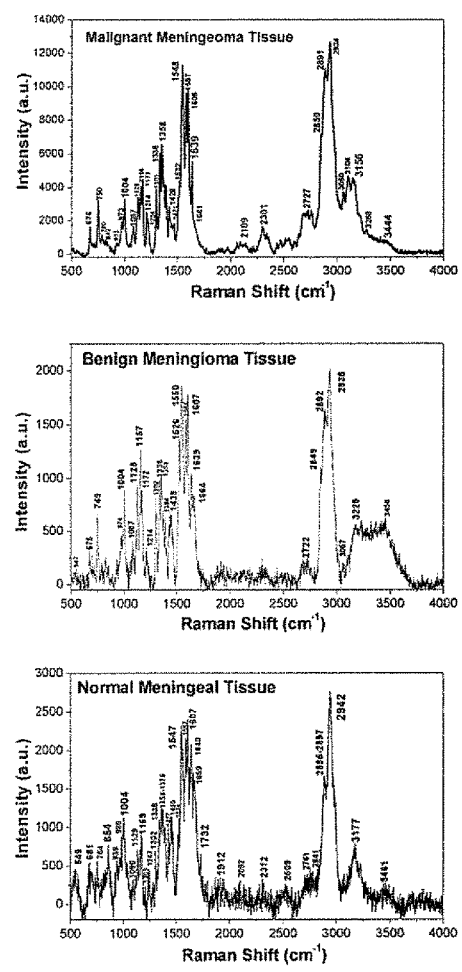
FIG. 6 is the graphic representations of signals produced under the RR conditions. The RR spectra recorded from three types of meningeal tissues. The Raman spectra showed from top to bottom as the Raman spectrum of malignant meningioma tissue, grade III (top); the Raman spectrum of meningioma benign tissue (center) and Raman spectrum of normal meningeal tissue (bottom).

FIG. 6 shows RR spectra recorded from three types of meningeal tissues. The Raman spectra showed from top to bottom as the Raman spectrum of malignant meningioma tissue, grade III (top); the Raman spectrum of meningioma benign tissue (center) and Raman spectrum of normal meningeal tissue (bottom).

Figure 7:
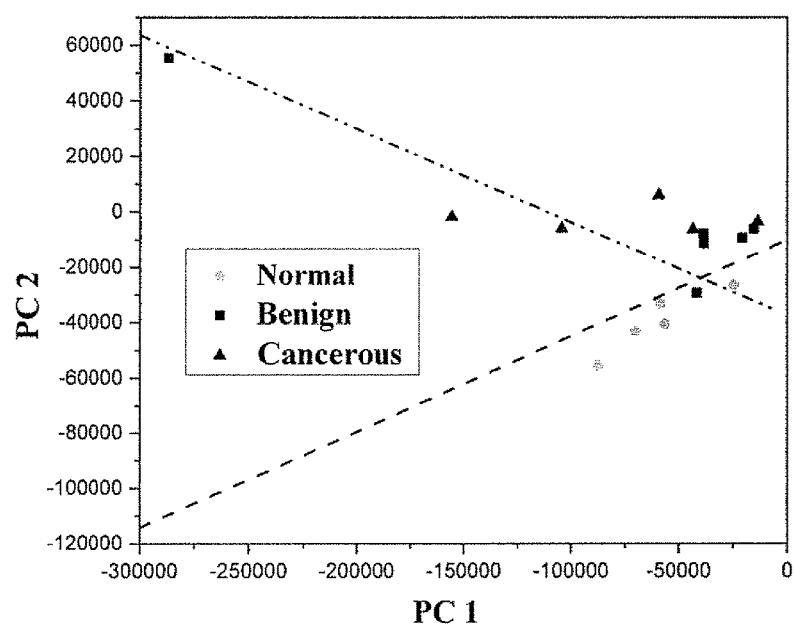
FIG. 7 is the graphic representations of signals produced under the RR conditions. The scatter plot of the posterior probability of classification for the malignant (stage III), benign and normal meningeal brain tissues were using PC1 and PC4 as diagnostically significant components. The separating lines were calculated using SVM algorithm, which yields a diagnostic sensitivity of 90.9% and specificity of 100% for identifying cancer from benign and normal brain tissue.

FIG. 7 shows a scatter plot of the posterior probability of classification for the malignant (stage II), benign and normal meningeal brain tissues were using PC1 and PC4 as diagnostically significant components. The separating lines were calculated using SVM algorithm, which yields a diagnostic sensitivity of 90.9% and specificity of 100% for identifying cancer from benign and normal brain tissue.

While the invention has been shown and described with reference to certain embodiments thereof, it will be understood by those skilled in the art that various changes in form and detail may be made therein without departing from the spirit and scope of the invention as defined by the appended claims and their equivalents.

The invention claimed is:

1. An apparatus for detecting clinical in vivo and in vitro lesions comprising a fiber-optical resonant Raman (RR) imaging endoscope system using a fiber optic probe for RR for detection of lesions and lesion regions or sites of cancer by measuring RR of molecule fingerprint modes to determine the presence of lesion regions or sites in human tissue, wherein a light source used for RR is selected from a group comprising a single mode laser having a wavelength at 532 nm, a laser with wavelengths <650 nm, Argon (514 nm, 488 nm, N2 laser, He Cd, fiber lasers, semiconductor lasers, Dye, or solid state lasers (with SHG of YAG 532 nm, and Ti: Sapphire with SHG (350 nm to 550 nm) to pump tissue molecules for RR imaging point, 2D and 3D.

2. An apparatus as defined in claim 1, wherein a probe of said system consists of a single mode optical fiber delivering both the excitation beam and the RR scattered signal light with optical filters.

3. An apparatus as defined in claim 2, wherein a balloon/umbrella end unit is attached at the distal end and side of said probe.

4. An apparatus as defined in claim 2, wherein a ball lens is coupled to a miniature high-resolution RR probe.

5. An apparatus as defined in claim 1, wherein RR spectral backscattering signal comprises an optical collection with spectrograph.

6. An apparatus as defined in claim 1, wherein a CCD camera with a notch filter is used at a laser frequency and holographic narrow band filters and system and fiber and filters.

7. An apparatus as defined in claim 1, wherein said imaging system comprises a compact RR ratio meter comprising narrow band filters; semiconductor diode lasers, optical filtered fibers at two lines and at laser line narrow band 2 or more optical filters at lipid, protein, glucose, DNA and tissue spectral regions, and multiple channel detectors; and a computer programmed to determine the ratios of one or more peaks of RR frequencies to detect lesions in at least one of the following wavelengths about 750 cm$^{-1}$, 1004 cm$^{-1}$, 1156 cm$^{-1}$, 1358 cm$^{-1}$, 1589 cm$^{-1}$, and bands at 2850 cm$^{-1}$, 2935 cm$^{-1}$ and transformed cells region to determine the presence of cancer and/or invasive lesions.

8. An apparatus as defined in claim 1, for a 2D and 3D sample, comprising a three-part Raman spectroscopic system, the light laser source comprising single mode lasers having wavelengths selected from a group comprising 532 nm, 514.5 nm and 488 nm, 785 nm and near IR wavelength; galvanometer mirror scanner for 2D and 3D RRS images, backscattering signal optical fiber collection with spectrograph, CCD camera; and a micro Raman imaging endoscope system.

9. An apparatus as defined in claim 1, wherein a light source used for RR is selected from the group comprising a laser providing the light at 532 nm (SHG Yag), 488 nm, 514 nm, 325 nm and 442 nm (He-Cd laser), and 408 nm as excitation sources for biomolecules in tissue to enhance the vibrations in RRS.

* * * * *